United States Patent [19]

Zima et al.

[11] Patent Number: 5,565,590
[45] Date of Patent: Oct. 15, 1996

[54] PROCESS FOR RECYCLING AMINO-CARBOXYLIC ACID WASTE MATERIALS INTO AMIDO-CARBOXYLIC ACIDS

[75] Inventors: George C. Zima, Kingsport; Gary P. Lutz, Church Hill, both of Tenn.; Gary W. McChesney, Batesville, Ark.; T. Hugh Williams, Fall Branch, Tenn.

[73] Assignee: Eastman Chemical Company, Kingsport, Tenn.

[21] Appl. No.: 334,899

[22] Filed: Nov. 7, 1994

[51] Int. Cl.[6] .................................................. C07C 231/00
[52] U.S. Cl. .............................. 554/69; 554/68; 554/70; 554/177; 554/179
[58] Field of Search ........................... 554/68, 70, 177, 554/69, 179

[56] References Cited

U.S. PATENT DOCUMENTS

| 2,453,234 | 11/1948 | Koch | 260/534 |
| 2,956,068 | 10/1960 | Dohr et al. | 260/404.5 |
| 4,605,762 | 8/1986 | Mandoki | 562/483 |
| 5,169,870 | 12/1992 | Corbin et al. | 521/42.8 |

FOREIGN PATENT DOCUMENTS 648889  8/1946  United Kingdom.

OTHER PUBLICATIONS

Kusunase et al., Chemical Abstracts, vol. 82, No. 10, 1975, p. 83, 591565.
*Indian Journal of Fibre & Textile Research*, vol. 16, Mar. 1991, pp. 46–51, India.

Primary Examiner—Gary Geist
Assistant Examiner—Deborah D. Carr
Attorney, Agent, or Firm—John D. Thallemer; Harry J. Gwinnell

[57] ABSTRACT

This invention relates to a process for recycling waste material selected from amino-carboxylic acid oligomers or polymers and amido-carboxylic acid oligomers or polymers into amido-carboxylic acids. A mixture containing water, an oligomeric or polymeric waste material, and a carboxylic acid is heated. The mixture is cooled to obtain a two phase system containing an aqueous phase and an organic phase which are separated. Carboxylic acids, unreacted starting materials, and the monomeric amido-carboxylic acid product are distilled from the organic phase. The remaining solid residue composed of high boiling oligomeric amino-carboxylic acids is recycled into Step (A).

20 Claims, No Drawings

5,565,590

1

PROCESS FOR RECYCLING AMINO-CARBOXYLIC ACID WASTE MATERIALS INTO AMIDO-CARBOXYLIC ACIDS

FIELD OF INVENTION

This invention relates to a process for recycling waste material selected from amino-carboxylic acid oligomers or polymers and amido-carboxylic acid oligomers or polymers into amido-carboxylic acids.

BACKGROUND OF THE INVENTION

Amido-carboxylic acids are industrial chemical intermediates for the preparation of many chemicals used in commerce. Amido-carboxylic acids are prepared by reacting a lactam with a carboxylic acid. Amido-carboxylic acids are also prepared by reacting a carboxylic acid, carboxylic acid chloride, carboxylic acid anhydride or carboxylic acid ester with an amino-carboxylic acid. These processes which form amido-carboxylic acids are referred to as amidation reactions.

It is known to convert lactams by hydrolysis into the corresponding amino-carboxylic acids in the presence of hydrolysis promoting reagents such as hydrochloric acid. However, pure amino-carboxylic acids are not directly obtained. In the case where hydrochloric acid is used as the promoting reagent, the amino-carboxylic acid hydrochloride is obtained and the separation of the free amino-carboxylic acid is cumbersome and expensive.

U. S. Pat. No. 2,453,234 discloses a process for preparing an amino-carboxylic acid by hydrolyzing a lactam by means of at least 10 moles of water per mole of lactam to produce an amino-carboxylic acid. Great Britain Pat. No. 648,889 discloses a process for preparing amino-carboxylic acids by heating aliphatic or cyclo-aliphatic lactams in the presence of more than 20 moles of water per mole of lactam. U.S. Pat. No. 2,956,068 discloses a process for preparing amido-carboxylic acids by reacting a lactam with a free carboxylic acid in the presence of catalytic amounts of water. The reaction product is obtained as a solid crystal mass which is subsequently suspended in water and neutralized. The reaction product contains significant quantities of oligomeric amido-carboxylic acids which are made up of a carboxylic acid chain and two or more repeating amino-carboxylic acid units. These oligomeric amido-carboxylic acids are undesirable for many applications.

U.S. patent application Ser. No. 08/228,611 discloses an aqueous process for preparing amido-carboxylic acids wherein lactam hydrolysis, carboxylic acid ester hydrolysis, and amidation reactions are conducted simultaneously. The process involves heating water, a lactam or an amino-carboxylic acid, and a carboxylic acid or ester to form a reaction mixture which is cooled to obtain a two phase system containing an aqueous phase and an organic phase. The organic phase containing the amido-carboxylic acid is separated from the aqueous phase. The reaction product contains significant quantities of oligomeric amido-carboxylic acids which are made up of a carboxylic acid chain and two or more repeating amino-carboxylic acid units. These oligomeric amido-carboxylic acids are undesirable for many applications.

Waste materials are also generated when monomeric amino-carboxylic acids are polymerized. For example, the manufacture of nylon 6 polymer (polycaproamide), produces about 8–10% low molecular weight oligomers

2

(extractables) as waste. The manufacture of nylon 6 fiber generates about 5–12% solid waste. According to the *Indian Journal of Fibre & Textile Research*, Vol. 16, March 1991, pp. 46–51, India generates about 7000–8000 metric tonnes of solid waste (nylon 6) every year. Thus, it is desirable for economic and environmental reasons to recycle the extractables and the solid waste.

U.S. Pat. No. 4,605,762 discloses a process for depolymerizing condensation polymers. The process involves subjecting condensation polymer waste material to aqueous hydrolysis in a hydrolysis zone, introducing high pressure steam into the hydrolysis zone below the level where the polymer waste material is introduced, and withdrawing an aqueous solution of the products of the hydrolysis reaction from an upper portion of the hydrolysis zone.

U.S. Pat. No. 5,169,870 discloses a process for recovering caprolactam from nylon 6 carpet. The process involves breaking the carpet down into scrap containing nylon 6 and non-nylon 6 backing materials. The scrap is fed into a depolymerizing reactor where the scrap is subjected to a depolymerization catalyst, temperatures of at least the melting point of nylon 6 and superheated steam to produce a caprolactam containing distillate. The caprolactam in the distillate is separated from other volatiles.

SUMMARY OF THE INVENTION

The present invention involves a process for recycling amino-carboxylic acid and amido–carboxylic acid oligomeric or polymeric waste materials into amido-carboxylic acids, said process comprising the steps of:

(A) reacting in a vessel at a temperature of 150° C. to 300° C. for 0.1 to 10 hours, a mixture containing (1) an oligomeric or polymeric waste material selected from the group consisting of amino-carboxylic acid oligomers or polymers having one or more lactam or amino-carboxylic acid repeating unit, amido-carboxylic acid oligomers or polymers having one or more lactam or amino-carboxylic acid repeating unit, and combinations thereof;

(2) 0.25 to 10 equivalents of a carboxylic acid compound per equivalent weight of amino-carboxylic acid contained in the amino-carboxylic acid oligomeric or polymeric waste material, said carboxylic acid compound having 6 to 26 carbon atoms selected from the group consisting of a carboxylic acid, a carboxylic acid ester and combinations thereof; and (3) 0.001 to 50 equivalents of water per equivalent weight of amino-carboxylic acid contained in the amino-carboxylic acid oligomeric or polymeric waste material, to form a reaction mixture containing an amido-carboxylic acid; and (B) cooling the reaction mixture formed in Step (A) to a temperature to achieve phase separation of an organic phase containing the amido-carboxylic acid, and an aqueous phase;

(C) separating the amido-carboxylic acid containing organic phase from the aqueous phase;

(D) isolating monomeric amido-carboxylic acid from the organic phase by a two stage distillation wherein the first stage involves removing low boiling components including water, carboxylic acids, amino-carboxylic acids and lactams, and the second stage involves removing monomeric amido-carboxylic acid, which leaves a residue of amido-carboxylic acid oligomers and polymers; and (E) recycling into Step (A) the low boiling components collected in the first stage of the distillation along with the residue of amido-carboxylic acid oligomers and polymers from Step (D).

DESCRIPTION OF THE INVENTION

The process of the present invention involves recycling amino-carboxylic acid and amido-carboxylic acid oligomeric or polymeric waste materials into amido-carboxylic acids. The term "recycling" for purposes of this invention means the practice of returning a portion of the reaction products to the first step in the process for the purpose of more efficient conversion of unreacted components and to consume undesirable reaction byproducts. The term "recycling" also includes recovery and reuse of waste or scrap materials generated from processes other than those defined by the claims of the present invention. The term "amido" for purposes of the present invention refers to compounds having at least one amino-carboxylic acid repeating unit and one carboxylic acid terminal group.

The process of the present invention involves at least one step. In Step (A), an oligomeric or polymeric waste material selected from an amino-carboxylic acid oligomer or polymer or an amido-carboxylic acid oligomer or polymer, a carboxylic acid or ester, and water are combined in a reactor. The reactor must be able to be heated and must contain the pressure of the reaction. Preferably, the reactor is an autoclave. The reaction in Step (A), involves up to three of the following independent reactions which occur simultaneously: hydrolysis of the carboxylic acid ester forming a carboxylic acid and an alcohol, hydrolysis of the amino-carboxylic acid oligomeric or polymeric waste material forming an amino-carboxylic acid, hydrolysis of the oligomeric amido-carboxylic acid forming amino-carboxylic acids and carboxylic acid, and amidation of the carboxylic acid with an amino-carboxylic acid to form an amido-carboxylic acid. The alcohol formed by the hydrolysis of the carboxylic acid ester is removed by methods known in the art such as distillation.

Component (1) is an oligomeric or polymeric waste material selected from amino-carboxylic acid oligomers or polymers having one or more lactam or amino-carboxylic acid repeating unit, or from amido-carboxylic acid oligomers or polymers having one or more lactam or amino-carboxylic acid repeating unit. The waste material may include combinations or mixtures of amino-carboxylic acids and amido-carboxylic acids. The amino-carboxylic acid repeating unit has the general formula $NH_2(CRR')_nCOOH$ and is characterized by a basic amino group ($NH_2$) and an acidic carboxyl group (COOH). The letter n in the formula is 1–26, preferably 1–10. The R and R' groups are independently selected from hydrogen, unsubstituted or substituted straight chain or branched $C_1$–$C_{20}$ alkyl, unsubstituted or substituted $C_3$–$C_8$ cycloalkyl, $C_3$–$C_8$ alkenyl, $C_3$–$C_8$ alkynyl, and $C_6$–$C_{14}$ aryl.

The unsubstituted and substituted $C_3$–$C_8$ cycloalkyl groups mentioned above refer to cycloaliphatic hydrocarbon groups which contain 3 to 8 carbons in the ring, preferably 5 or 6 carbons, and these cycloalkyl groups substituted with one or two of $C_1$–$C_4$ alkyl, $C_1$–$C_4$ alkoxy, hydroxy or $C_1$–$C_4$ alkanoyloxy.

The $C_3$–$C_8$ alkenyl and $C_3$–$C_8$ alkynyl groups represent straight or branched chain hydrocarbon radicals containing 3 to 8 carbons in the chain and which contain a carbon-carbon double bond or a carbon-carbon triple bond, respectively.

The term "aryl" is used to include carbocyclic aryl groups containing up to fourteen carbons, e.g., phenyl and naphthyl, and those substituted with one or two groups selected from $C_1$–$C_4$-alkyl, $C_1$–$C_4$ alkoxy, $C_1$–$C_4$-alkoxycarbonyl, $C_1$–$C_4$-alkanoyloxy, $C_1$–$C_4$-alkanoylamino, halogen, cyano, $C_1$–$C_4$-alkylsulfonyl, $C_1$–$C_4$-alkylene-$(OH)_n$, $O$-$C_1$–$C_4$-alkylene-$(OH)_n$, —S-$C_1$–$C_4$-alkylene-$(OH)_n$, —$SO_2$-$C_1$–$C_4$-alkylene-$(OH)_n$, —$CO_2$-$C_1$–$C_4$-alkylene-$(OH)_n$, $SO_2N(R_{17})C_1$–$C_4$-alkylene-$(OH)_n$, —$SO_2N(C_1$–$C_4$-alkylene-$OH)_2$, —$CON(R_{17})$ $C_1$–$C_4$-alkylene-$(OH)_n$, —$CON(C_1$–$C_4$-alkylene-$OH)_2$, —$N(SO_2C_1$–$C_4$-alkyl)-alkylene-$(OH)_n$ or —$N(SO_2phenyl)$-$C_1$–$C_4$-alkylene-$(OH)_n$; wherein n is one or two.

The term "aryl" is also used to include heterocyclic aryl groups such as a 5 or 6-membered heterocyclic aromatic ring containing one oxygen atom, and/or one sulfur atom, and/or up to three nitrogen atoms, said heterocyclic aryl ring optionally fused to one or two phenyl rings or another 5 or 6-membered heteroaryl ring. Examples of such ring systems include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-[1,5-b]pyridazinyl and purinyl, benzoxazolyl, benzothiazolyl, benzimidazolyl, indolyl, and the like and those rings substituted with one or more substituents listed above in the definition of the term "aryl".

In addition, the term "aryl" includes arylene groups. The term "arylene" is used to represent a divalent carbocyclic aryl hydrocarbon moiety containing up to fourteen carbons, e.g., o-, m- and p-phenylene, and those substituted with one or two groups selected from $C_1$–$C_4$-alkyl, $C_1$–$C_4$-alkoxy or halogen. Preferably, the oligomeric or polymeric waste material is selected from an oligomer generated during the manufacture of polycaproamide or polycaproamide itself.

Component (2) is a carboxylic acid compound. The carboxylic acid compound is a carboxylic acid or carboxylic acid ester, or combination thereof, which contains an aliphatic radical with a straight or branched chain, a cycloaliphatic radical, or a hydroaromatic radical. The carboxylic acid or carboxylic acid ester has 6–26 carbon atoms, preferably 8–20 carbon atoms, and most preferably 8–10 carbon atoms. These radicals may be connected to the carboxyl group through an aromatic radical. The carboxylic acids and carboxylic acid esters may be straight or branched chain fatty acids of natural or synthetic origin which may be of a saturated or unsaturated nature. The carboxylic acids and esters can contain more than one carboxylic acid or ester group. Esters of carboxylic acids include, but are not limited to, the methyl, ethyl, propyl, and butyl ester of a carboxylic acid. The carboxylic acids and carboxylic acid esters may be used in pure form or else in the form of their mixtures as commercially available.

Examples of carboxylic acids and carboxylic acid esters are: caprylic acid, methyl caprylate, pelargonic acid, methyl pelargonate, capric acid, methyl caprate, isopropyl caprate, undecylic acid, lauric acid, palmitic acid, stearic acid, oleic acid, linoleic acid, behenic acid, terephthalic acid, dimethyl terephthalate, phthalic acid, isophthalic acid, naphthalene-2,6dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, and the like. Preferred carboxylic acids are capric, pelargonic and caprylic. Preferred carboxylic acid esters are methyl caprate, methyl pelargonate and methyl caprylate.

Component (3) is water which may arise from any source and includes tap water, distilled water, and water that is present in any other component of the reaction mixture.

Distilled water is preferred since tap water may contain metal salts which in combination with the carboxylic acid could form surface active agents and inhibit isolation of the product. The water for use as component (3) may be present in an aqueous suspension of the oligomeric or polymeric waste material. In addition, the water for use as component (3) may be present in the carboxylic acid compound. It is important to note that water is formed in the amidation reaction between a carboxylic acid and an amino-carboxylic acid, and such water is included as component (3).

Step (A) may also include a nitrogen containing compound, component (4), which is selected from a lactam or an amino-carboxylic acid. The nitrogen containing compounds may be recycled into Step (A) as low boiling components which are collected in a distillation or crystallization step during purification of the amido-carboxylic acid product. Suitable lactam monomers contain at least 3 carbon atoms per molecule, preferably 4 to 7 carbon atoms per molecule. Suitable lactam monomers include butyrolactam, valerolactam, epsilon-caprolactam, beta-propiolactam, delta-valerolactam, and similar lactams. These lactams may be substituted at the nitrogen atom by lower hydrocarbon radicals containing for example, 1–3 carbon atoms. For example, methylcaprolactam may be used. Epsilon-caprolactam and substituted derivatives thereof are the preferred lactam monomers. The amino-carboxylic acid has the same structure as described for the amino-carboxylic acid repeating unit of component (1).

Step (A) may also include an acid catalyst in addition to the carboxylic acid, component (2), to increase the speed of the reactions. Suitable catalysts include carboxylic acids such as acetic acid or mineral acids such as sulfuric acid. Small quantities of the catalyst are sufficient, such as from 0.0001% to 1% based on the weight of the reactants in the reaction mixture.

The reaction of Step (A) may be carried out over a wide range of temperatures and times. Temperatures below 150° C. are not preferred since the rate of hydrolysis may be very slow. In addition, temperatures above 300° C. are not preferred since competing decomposition reactions of the monomeric materials may take place. Accordingly, a temperature between 150° to 300° C. is preferred. Most preferably, Step (A) is conducted at a temperature of 200° C. to 250° C. in the substantial absence of oxygen. The time of the reaction should be sufficient to form amido-carboxylic acids. Preferably, the time of reaction in Step (A) is 0.1 to 10 hours, more preferably 1 to 4 hours. However, it is within the scope of this invention to use times and temperatures outside of the preferred ranges.

The carboxylic acid compound is present in an amount of 0.25 to 10 equivalents, preferably, 1 to 5 equivalents per equivalent weight of amino-carboxylic acid in the oligomeric or polymeric waste material. Most preferably, the carboxylic acid compound is present in an amount of 2 to 4 equivalents per equivalent weight of amino-carboxylic acid in the oligomeric or polymeric waste material. Insufficient carboxylic acid increases the fraction of oligomeric amido-carboxylic acids while decreasing the fraction of monomeric amido-carboxylic acid product. Although there is no critical higher limit to the amount of carboxylic acid compound, in practice one will not use a higher ratio than is strictly necessary to produce the desired results in any given case since to do so would render the process unnecessarily expensive from the point of view of recovering the desired product in pure form.

Water is present in an amount of 0.001 to 50 equivalents per equivalent weight of amino-carboxylic acid in the oligomeric or polymeric waste material. In the case where phase separation is desired, the amount of water required should be in excess of that which is soluble in the reaction mixture organic phase at the temperature of phase separation. Water is preferably present in an amount of 20 to 40 equivalents per equivalent weight of amino-carboxylic acid in the oligomeric or polymeric waste material. The addition of water allows the ratio of the equivalents of carboxylic acid per equivalent weight of amino-carboxylic acid in the waste material to be substantially lower by hydrolysing the oligomeric or polymeric amino-carboxylic acids.

Insufficient water results in the polymerization of monomeric materials. Although there is no critical higher limit to the amount of water, the use of greater than 50 equivalents per equivalent weight of amino-carboxylic acid in the oligomeric or polymeric waste material creates a situation where it is increasingly difficult to separate the small organic phase from the aqueous phase and would render the process unnecessarily expensive from the point of view of recovering the desired product in pure form. If not enough water is used, the solubility of water in the organic phase precludes the formation of two phases.

If desired, a two phase system containing an aqueous phase and an organic phase is prepared, Step (B). The reaction mixture generated in Step (A) is cooled to a temperature which is above the freezing point of the components of the reaction mixture. The temperature at which the aqueous phase and organic phase separate depends on the specific reactants, however, generally a temperature of less than 150° C. is required for phase separation. Preferably, the reaction mixture is cooled to a temperature of less than 100° C. and most preferably, 70°–90° C. Step (B) may be conducted in the same vessel as Step (A) in a batch process, or Step (B) may be conducted in a separate vessel using either a batch process or a continuous process. Cooling is accomplished by methods known in the art such as external cooling with water, ice or through the use a cooling jacket. The amino-carboxylic acids which are soluble in water become miscible with the organic phase at the reaction temperatures. In contrast, the carboxylic acids which are not soluble in water become at least partially miscible with the water phase at the reaction temperatures. Miscibility of the phases allows the reaction to proceed more readily. Phase separation occurs upon cooling. For the most part, the carboxylic acids remain in the organic phase and the amino-carboxylic acids, and lactams remain in the water phase, however, some amino-carboxylic acids, lactams and water are dissolved in the organic phase.

The two phase system generated in Step (B) can be separated by methods known in the art such as decantation or coalescence. Step (C) involves separation of the organic phase from the aqueous phase. Step (C) may be conducted in the same vessel as Step (A) and Step (B) in a batch process, or Step (C) may be conducted in a separate vessel using either a batch process or a continuous process.

Purification of the organic phase to recover the amido-carboxylic acid product is accomplished by methods known in the art such as distillation or crystallization. Preferably, a two-stage distillation is used in Step (D) to recover the amido-carboxylic acid product. In the first distillation stage, water, carboxylic acids and unreacted nitrogen containing compounds,.which are low boiling compounds relative to the amido-carboxylic acid product, are removed from the organic phase to provide an amido-carboxylic acid rich residue. In the second distillation stage, the temperature is increased, the pressure is decreased and the amido-carboxylic acid product is removed from the amido-carboxylic acid rich residue produced in the first stage of the distillation. The high boiling material which remains when the amido-carboxylic acid product is removed from the amido-carboxylic acid rich residue contains high levels of high boiling oligomeric amido-carboxylic acids.

The process of the present invention may also include a fifth step, Step (E), in which the high boiling oligomeric amido-carboxylic acid residue generated in Step (D) is recycled into Step (A) as waste material. Oligomeric or polymeric waste material from other sources may be combined with the residue from Step (D) to be used in Step (A). In addition, the low boiling compounds such as water, carboxylic acids and unreacted nitrogen containing compounds which were removed in Step (D) may be recycled into Step (A).

The process of the present invention will be further illustrated by a consideration of the following examples, which are intended to be exemplary of the invention.

EXAMPLE I

Octanoic Acid, 796 lbs., decanoic acid, 530 lbs., water, 1500 lbs., and caprolactam, 290 lbs., were mixed and heated to 225° C. to 230° C. in a 500 gallon stirred autoclave for 2 hours. The reaction mixture was cooled to 60° C. at which temperature phase separation occurred. The product was removed from the autoclave. The organic phase containing the product was isolated by decantation from the aqueous phase. The products in the organic phase were isolated by liquid-liquid phase separation to yield 1536 pounds or a 95% mass recovery yield of product mixture. Analytical data for the organic phase is summarized in Table I.

Example I shows that a mixture of octanoic acid, decanoic acid, and caprolactam are reacted in water to form an amido-carboxylic acid.

EXAMPLE II

The organic phase prepared in Example I was separated by distillation into a low boiling component containing carboxylic acids and unreacted nitrogen containing compounds, monomeric amido-carboxylic acid product, and high boiling oligomeric amido-carboxylic acids which remained in the vessel as waste residue. The composition of the amido-carboxylic acid product is listed in Table I as IIa. The composition of the oligomeric amido-carboxylic acid residue is listed in Table I as IIb.

Example II shows that monomeric amido-carboxylic acid product can be isolated from the first stage distillation residue.

EXAMPLE III

The oligomeric amido-carboxylic acid residue obtained in Example II, 15.0 grams, was mixed with 84.4 grams of a mixture containing 60% octanoic acid and 40% decanoic acid and heated to 95° C. The test results are summarized in Table I.

EXAMPLE IV

The oligomeric amido-carboxylic acid residue prepared in Example II, 15.0 grams, was mixed with 84.4 grams of a mixture containing 60% octanoic acid and 40% decanoic acid and was heated to 210° C. in an open beaker. The reaction mixture was allowed to cool to room temperature. The test results are summarized in Table I.

Example IV shows that the analytical results for the reaction mixture prepared in Example III were not significantly changed by heating to 210° C. in the absence of added water.

EXAMPLE V

The oligomeric amido-carboxylic acid residue prepared in Example II, 15.0 grams, was mixed with 84.4 grams of a mixture containing 60% octanoic acid and 40% decanoic acid and with 100.7 grams of distilled water. The resulting mixture was heated for 1 hour at 230° C. in a rocking autoclave. After cooling to room temperature the organic phase was isolated. The test results are summarized in Table I.

Example V demonstrates that the addition of water and heating to 230° C. increases the yield of amido-carboxylic acid content of the organic phase, when compared to Examples III and IV.

EXAMPLE VI

The oligomeric amido-carboxylic acid residue prepared in Example II, 15.0 grams, was mixed with 84.4 grams of a mixture containing 60% octanoic acid and 40% decanoic acid and with 100.7 grams of distilled water. The resulting mixture was heated for 4 hour at 230° C. in a rocking autoclave. After cooling to room temperature the organic phase was isolated by decantation. The test results are summarized in Table I.

Example VI had a 4 hour reaction time as opposed to 1 hour for Example V. Similar analytical results were obtained for Examples V and VI.

EXAMPLE VII

Nylon 6 pellets, 18.7 grams, were combined with 84.4 grams of nonanoic acid and 100.7 grams of distilled water in a 300 ml rocking autoclave. The mixture was heated to 230° C. for one hour. After cooling, the organic phase was separated by decantation. The test results are summarized in Table I.

Example VII shows that waste materials containing nylon 6 can be recycled into amido-carboxylic acids.

EXAMPLE VIII

Nylon 6 pellets, 18.7 grams, were combined with 84.4 grams of nonanoic acid and 100.7 grams of distilled water in a 300 ml rocking autoclave. The mixture was heated to 230° C. for four hours. After cooling, the organic phase was separated by decantation. The test results are summarized in Table I.

Example VIII shows that amido-carboxylic acids can be obtained by the process of this invention employing a four hour reaction time at a temperature of 230° C.

EXAMPLE IX

Nylon 6 pellets, 18.7 grams, were combined with 84.4 grams of nonanoic acid and 100.7 grams of distilled water in a 300 ml rocking autoclave. The mixture was heated to 250° C. for four hours. After cooling, the organic phase was separated by decantation. The test results are summarized in Table I.

Example IX shows that amido-carboxylic acids can be obtained by the process of this invention employing a four hour reaction time at a temperature of 250° C.

EXAMPLE X

Nylon 6 pellets, 36.9 grams, were combined with 166.8 grams of nonanoic acid in a 300 ml rocking autoclave. The mixture was heated to 250° C. for eight hours, was cooled, and was isolated as a single organic phase. The water content of the resulting product was 0.045 equivalents per equivalent weight of the polymeric waste material (nylon 6). The test results are summarized in Table I.

Example X shows that amido-carboxylic acids can be obtained by the process of this invention without the use of any added water.

TABLE I

| Ex. | I | IIa/IIb | III | IV | V | VI | VII | VIII | IX | X |
|---|---|---|---|---|---|---|---|---|---|---|
| OA | 42.1 | ND/ND | 53.0 | 52.3 | 48.6 | 49.2 | | | | |
| NA | | | | | | | 72.2 | 74.4 | 72.5 | 71.4 |
| DA | 28.2 | ND/ND | 32.8 | 33.9 | 35.0 | 35.8 | | | | |
| $C_8AC$ | 11.7 | 69.4/17.0 | 2.8 | 3.2 | 6.0 | 6.3 | | | | |
| $C_9AC$ | | | | | | | 13.0 | 15.4 | 14.1 | 12.9 |
| $C_{10}AC$ | 6.4 | 33.0/15.7 | 2.4 | 2.8 | 3.2 | 3.3 | | | | |
| Total Monomeric Amido-Carboxylic Acid | 18.1 | 102.4/32.7 | 5.2 | 5.7 | 9.2 | 9.6 | 13.0 | 15.4 | 14.1 | 12.9 |
| Oligomeric Amido-Carboxylic Acid | 4.3 | 0.6/75.0 | 11.1 | 10.7 | 1.4 | 1.3 | 6.5 | 4.2 | 3.5 | 5.3 |
| CL | 4.1 | 0.69/0.04 | 0.06 | 0.07 | 2.6 | 2.8 | 5.3 | 5.6 | 5.8 | 5.9 |

OA = octanoic acid
DA = decanoic acid
NA = nonanoic acid
AC = amido caproic acid
CL = caprolactam
ND = none detected Many variations will suggest themselves to those skilled in this art in light of the above detailed description. All such obvious modifications are within the full intended scope of the appended claims.

What is claimed is:

1. A process for recycling amino-carboxylic acid and amido-carboxylic acid oligomeric or polymeric waste materials into amido-carboxylic acids, said process comprising reacting in a vessel a mixture containing:
   (1) an oligomeric or polymeric waste material selected from the group consisting of amino-carboxylic acid oligomers or polymers having one or more lactam or amino-carboxylic acid repeating unit, amido-carboxylic acid oligomers or polymers having one or more lactam or amino-carboxylic acid repeating unit, and combinations thereof;
   (2) 0.25 to 10 equivalents of a carboxylic acid compound per equivalent weight of amino-carboxylic acid contained in the amino-carboxylic acid oligomeric or polymeric waste material, said carboxylic acid compound having 6 to 26 carbon atoms selected from the group consisting of a carboxylic acid, a carboxylic acid ester and combinations thereof; and
   (3) 0.001 to 50 equivalents of water per equivalent weight of amino-carboxylic acid contained in the amino-carboxylic acid oligomeric or polymeric waste material,
   at a temperature of 150° C. to 300° C. and sufficient time to form a reaction mixture containing an amido-carboxylic acid.

2. The process of claim 1 wherein the oligomeric or polymeric waste material, component (1), is an oligomer generated during the manufacture of polycaproamide.

3. The process of claim 1 wherein the oligomeric or polymeric waste material, component (1), contains polycaproamide.

4. The process of claim 1 wherein Step (A) is conducted at a temperature of 150° C.–300° C. for 0.1 to 10 hours.

5. The process of claim 4 wherein Step (A) is conducted at a temperature of 200° C.–250° C. for 1 to 4 hours.

6. The process of claim 1 wherein the carboxylic acid, component (2), is selected from the group consisting of caprylic acid, pelargonic acid, capric acid, undecylic acid, lauric acid, palmitic acid, stearic acid, oleic acid, behenic acid, terephthalic acid, phthalic acid, isophthalic acid, naphthalene-2,6-dicarboxylic acid, cyclohexanedicarboxylic acid, cyclohexanediacetic acid, succinic acid, adipic acid, and sebacic acid.

7. The process of claim 6 wherein the carboxylic acid, component (2), is selected from the group consisting of capric acid and caprylic acid.

8. The process of claim 1 wherein the carboxylic acid ester, component (2), is selected from the group consisting of methyl caprylate, methyl caprate, methyl pelargonate, isopropyl caprate, and dimethyl terephthalate.

9. The process of claim 8 wherein the carboxylic acid ester is selected from the group consisting of methyl caprylate, methyl caprate, and methyl pelargonate.

10. The process of claim 1 wherein the carboxylic acid compound, component (2), is present in an amount of 1 to 5 equivalents per equivalent weight of amino-carboxylic acid in the oligomeric or polymeric waste material.

11. The process of claim 10 wherein the carboxylic acid compound, component (2), is present in an amount of 2 to 4 equivalents per equivalent weight of amino-carboxylic acid in the oligomeric or polymeric waste material.

12. The process of claim 1 wherein the water, component (3), is present in an amount of 1 to 50 equivalents per equivalent weight of amino-carboxylic acid in the oligomeric or polymeric waste material.

13. The process of claim 12 wherein the water is present in an amount of 20 to 40 equivalents per equivalent weight of amino-carboxylic acid in the oligomeric or polymeric waste material.

14. The process of claim 1 which additionally contains a nitrogen containing compound, component (4), which is selected from the group consisting of a lactam containing 3 to 7 carbon atoms per molecule, and an amino-carboxylic acid, provided the amino-carboxylic acid has the formula NH$_2$(CRR')$_n$COOH wherein n is 1–10, and R and R' are independently selected from the group consisting of hydrogen, unsubstituted or substituted C$_1$–C$_{20}$ alkyl, unsubstituted or substituted C$_3$–C$_8$ cycloalkyl, C$_3$–C$_8$ alkenyl, C$_3$–C$_8$ alkynyl, and C$_6$–C$_{14}$ aryl.

15. The process of claim 14 wherein the nitrogen containing compound is a lactam selected from the group consisting of butyrolactam, valerolactam, epsilon-caprolactam, beta-propiolactam, and delta-valerolactam.

16. The process of claim 15 wherein the lactam is epsilon-caprolactam.

17. A process for recycling amino-carboxylic acid and amido-carboxylic acid oligomeric or polymeric waste materials into amido-carboxylic acids, said process comprising the steps of:
(A) reacting in a vessel a mixture containing
  (1) an oligomeric or polymeric waste material selected from the group consisting of amino-carboxylic acid oligomers or polymers having one or more lactam or amino-carboxylic acid repeating unit, amido-carboxylic acid oligomers or polymers having one or more lactam or amino-carboxylic acid repeating unit, and combinations thereof;
  (2) 0.25 to 10 equivalents of a carboxylic acid compound per equivalent weight of amino-carboxylic acid contained in the amino-carboxylic acid oligomeric or polymeric waste material, said carboxylic acid compound having 6 to 26 carbon atoms selected from the group consisting of a carboxylic acid, a carboxylic acid ester and combinations thereof; and
  (3) 0.001 to 50 equivalents of water per equivalent weight of amino-carboxylic acid contained in the amino-carboxylic acid oligomeric or polymeric waste material, at a temperature Of 150° C. to 300° C. and sufficient time to form a reaction mixture containing an amido-carboxylic acid; and
(B) cooling the reaction mixture formed in Step (A) to a temperature to achieve phase separation of an organic phase containing the amido-carboxylic acid, and an aqueous phase;
(C) separating the amido-carboxylic acid containing organic phase from the aqueous phase; and
(D) isolating monomeric amido-carboxylic acid from the organic phase by a two stage distillation wherein the first stage involves removing low boiling components including water, carboxylic acids, amino-carboxylic acids and lactams, and the second stage involves removing monomeric amido-carboxylic acid.

18. A process for recycling amino-carboxylic acid and amido-carboxylic acid oligomeric or polymeric waste materials into amido-carboxylic acids, said process comprising the steps of:
(A) reacting in a vessel a mixture containing
  (1) an oligomeric or polymeric waste material selected from the group consisting of amino-carboxylic acid oligomers or polymers having one or more lactam or amino-carboxylic acid repeating unit, amido-carboxylic acid oligomers or polymers having one or more lactam or amino-carboxylic acid repeating unit, and combinations thereof;
  (2) 0.25 to 10 equivalents of a carboxylic acid compound per equivalent weight of amino-carboxylic acid contained in the amino-carboxylic acid oligomeric or polymeric waste material, said carboxylic acid compound having 6 to 26 carbon atoms selected from the group consisting of a carboxylic acid, a carboxylic acid ester and combinations thereof; and
  (3) 0.001 to 50 equivalents of water per equivalent weight of amino-carboxylic acid contained in the amino-carboxylic acid oligomeric or polymeric waste material, at a temperature of 150° C. to 300° C. and sufficient time to form a reaction mixture containing an amido-carboxylic acid; and
(B) cooling the reaction mixture formed in Step (A) to a temperature to achieve phase separation of an organic phase containing the amido-carboxylic acid, and an aqueous phase;
(C) separating the amido-carboxylic acid containing organic phase from the aqueous phase; and
(D) isolating monomeric amido-carboxylic acid from the organic phase by crystallization.

19. A process for recycling amino-carboxylic acid and amido-carboxylic acid oligomeric or polymeric waste materials into amido-carboxylic acids, said process comprising the steps of:
(A) reacting in a vessel at a temperature of 150° C. to 300° C. for 0.1 to 10 hours, a mixture containing
  (1) an oligomeric or polymeric waste material selected from the group consisting of amino-carboxylic acid oligomers or polymers having one or more lactam or amino-carboxylic acid repeating unit, amido-carboxylic acid oligomers or polymers having one or more lactam or amino-carboxylic acid repeating unit, and combinations thereof;
  (2) 0.25 to 10 equivalents of a carboxylic acid compound per equivalent weight of amino-carboxylic acid contained in the amino-carboxylic acid oligomeric or polymeric waste material, said carboxylic acid compound having 6 to 26 carbon atoms selected from the group consisting of a carboxylic acid, a carboxylic acid ester and combinations thereof; and
  (3) 0.001 to 50 equivalents of water per equivalent weight of amino-carboxylic acid contained in the amino-carboxylic acid oligomeric or polymeric waste material, to form a reaction mixture containing an amido-carboxylic acid; and
(B) cooling the reaction mixture formed in Step (A) to a temperature to achieve phase separation of an organic phase containing the amido-carboxylic acid, and an aqueous phase;
(C) separating the amido-carboxylic acid containing organic phase from the aqueous phase;
(D) isolating monomeric amido-carboxylic acid from the organic phase by a two stage distillation wherein the first stage involves removing low boiling components including water, carboxylic acids, amino-carboxylic acids and lactams, and the second stage involves removing monomeric amido-carboxylic acid, which leaves a residue of amino-carboxylic acid oligomers and polymers; and
(E) recycling into Step (A) the low boiling components collected in the first stage of the distillation along with the residue of amido-carboxylic acid oligomers and polymers from Step (D).

20. A process for recycling amino-carboxylic acid and amido carboxylic acid oligomeric acid oligomeric or polymeric waste materials into amido-carboxylic acids, said process comprising the steps of:
(A) reacting in a vessel at a temperature of 150° C. to 300° C. for 0.1 to 10 hours, a mixture containing
  (1) an oligomeric or polymeric waste material selected from the group consisting of amino-carboxylic acid oligomers or polymers having one or more lactam or amino-carboxylic acid repeating unit, amido-carboxylic acid oligomers or polymers having one or more lactam or amino-carboxylic acid repeating unit, and combinations thereof;

(2) 0.25 to 10 equivalents of a carboxylic acid compound per equivalent weight of amino-carboxylic acid contained in the amino-carboxylic acid oligomeric or polymeric waste material, said carboxylic acid compound having 6 to 26 carbon atoms selected from the group consisting of a carboxylic acid, a carboxylic acid ester and combinations thereof;

(3) 0.001 to 50 equivalents fo water per equivalent weight of amino-carboxylic acid contained in the amino-carboxylic acid oligomeric or polymeric waste material, to form a reaction mixture containing an amido-carboxylic acid; and (4) a nitrogen containing compound selected from the group consisting of a lactam containing 3 to 7 carbon atoms per molecule, and an amino-carboxylic acid, provided the amino-carboxylic acid has the formula $NH_2(CRR')_nCOOH$ wherein n is 1–10, and R and R' are independently selected from the group consisting of hydrogen, unsubstituted or substituted $C_1$–$C_{20}$ alkyl, unsubstituted or substituted $C_3$–$C_8$ cycloalkyl, $C_3$–$C_8$ alkenyl, $C_3$–$C_8$ alkynyl, and $C_6$–$C_{14}$ aryl; and (B) cooling the reaction mixture formed in Step (A) to a temperature to achieve phase separation of an organic phase containing the amido-carboxylic acid, and an aqueous phase;

(C) separating the amido-carboxylic acid containing organic phase from the aqueous phase;

(D) isolating monomeric amido-carboxylic acid from the organic phase by a two stage distillation wherein the first stage involves removing low boiling components including water, carboxylic acids, amino-carboxylic acids and lactams, and the second stage involves removing monomeric amido-carboxylic acid, which leaves a residue of amido-carboxylic acid oligomers and polymers; and (E) recycling into Step (A) the low boiling components collected in the first stage of the distillation along with the residue of amido-carboxylic acid oligomers and polymers from Step (D).

* * * * *